(12) United States Patent
Müller

(10) Patent No.: US 6,478,967 B1
(45) Date of Patent: Nov. 12, 2002

(54) REMOVAL OF CONTAMINANTS FROM BIOLOGICAL PRODUCTS

(75) Inventor: Egbert Müller, Darmstadt (DE)

(73) Assignee: Merck Patent Gesellschaft MIT, Darmstadt (DE)

( * ) Notice: Subject to any disclaimer, the term of this patent is extended or adjusted under 35 U.S.C. 154(b) by 0 days.

(21) Appl. No.: 09/623,983

(22) PCT Filed: Mar. 2, 1999

(86) PCT No.: PCT/EP99/01353

§ 371 (c)(1),
(2), (4) Date: Dec. 20, 2000

(87) PCT Pub. No.: WO99/47227

PCT Pub. Date: Sep. 23, 1999

(30) Foreign Application Priority Data

Mar. 13, 1998 (DE) ......................................... 198 10 947

(51) Int. Cl.[7] .............................................. B01D 61/14
(52) U.S. Cl. ..................... 210/650; 210/651; 210/683; 436/178; 521/27
(58) Field of Search ................................ 210/638, 650, 210/651, 653, 654, 679, 683, 685, 500.37, 500.38, 502.1; 521/27; 436/178; 435/30, 31, 311

(56) References Cited

U.S. PATENT DOCUMENTS

| | | | | |
|---|---|---|---|---|
| 4,431,545 A | * | 2/1984 | Pall et al. ................... | 210/650 |
| 4,693,828 A | * | 9/1987 | Yoshioko et al. ........... | 210/679 |
| 4,711,793 A |   | 12/1987 | Ostreicher et al. | |
| 4,915,839 A | * | 4/1990 | Marionaccio et al. .. | 210/500.38 |
| 5,438,128 A |   | 8/1995 | Nieuwkerk et al. | |
| 5,531,893 A | * | 7/1996 | Hu et al. ................ | 210/500.37 |
| 6,319,404 B1 | * | 11/2001 | Zhang et al. .......... | 210/500.38 |

FOREIGN PATENT DOCUMENTS

| | | |
|---|---|---|
| DE | 195 43 371 | 5/1997 |
| GB | 1 092 754 | 11/1967 |
| WO | 93 08894 | 5/1993 |

\* cited by examiner

Primary Examiner—Joseph W. Drodge
(74) Attorney, Agent, or Firm—Millen, White, Zelano & Branigan, P.C.

(57) ABSTRACT

The invention relates to methods for separating biological contaminants (viruses, nucleic acids and/or endotoxins) from biological products, or for reducing the content of such biological contaminants in said biological products. The sample (biological product) to be purified is treated with an anion exchanger membrane. Said anion exchanger membrane is obtained by reacting a polyamide with an aminoreactive compound which is capable of polymerisation. This is followed by polymerisation with monomers which contain cationic groups or into which cationic groups can be introduced in a reaction analogous to polymerisation.

5 Claims, 1 Drawing Sheet

REMOVAL OF CONTAMINANTS FROM BIOLOGICAL PRODUCTS

The invention relates to processes for eliminating contaminants from biological products by separation using anion-exchange membranes and to biological products cleaned up using these processes.

High demands are made of the purity of biological products, especially if they are to be used, for example, for pharmaceutical purposes. This is true especially if intraperitoneal or intravenous applications are contemplated. In this connection, especially viruses, endotoxins and nucleic acids, such as DNA, are of importance as possible contaminants. These contaminants are summarized as biological contaminants.

Contaminating viruses can be made harmless, for example, by chemical inactivation; WO 95/16 030 describes process variants which are customary in this context. Furthermore, removal by ultrafiltration is customary; for this purpose, for example, EP 0 302 949 discloses an ultrafiltration membrane having a specific pore geometry. Removal specifically of human immuno-deficiency virus (HIV) on non-porous ion-exchange materials is disclosed in EP 0 320 184. Endotoxins can be removed by treatment with a salt-containing detergent solution, as disclosed, for example, in WO 95/21 179. For the removal of endotoxins, furthermore, membranes derivatized in a special manner are proposed (WO 97/33 683). Nucleic acids can be removed by particulate anion exchangers, as described, for example, in J. Chromat. A, 658, pages 459–463 (1994).

WO 96/22 316 and WO 97/49 754 disclose polyamide-based adsorption membranes having improved properties. These improved separation materials may be synthesized by reacting the aminogroups of a polyamide with an amino-reactive compound or by reacting the carboxyl groups of a polyamide with a carboxyl-reactive compound, polymerizable groups being introduced into the abase, polymer. Additional amino groups or carboxyl groups can be introduced prior to the introduction of the polymerizable groups by reacting with diamines or dicarboxylic acids or dicarboxylic acid derivatives. Monomers can then be polymerized onto the said polymerizable groups. These monomers can comprise separation effectors; it is also possible to introduce separation effectors into the monomer units using known polymer-analogous reactions. With regard to the possible separation effectors and the preparation of adsorption membranes which comprise these separation effectors, reference is made to the abovementioned publications. The separation effectors mentioned in these publications also include cationic groups. The use of the anion-exchange membranes as disclosed in WO 96/22 316 and WO 97/49 754 for removing biological contaminants from biological products is the subject-matter of the present invention. For the inventive use, preference is given especially to anion-exchange membranes which are obtainable by reaction of a polyamide with a amino-reactive polymerizable compound and subsequent polymerization with monomers which comprise cationic groups, or into which cationic groups can be introduced in a polymer-analogous reaction.

These anion-exchange membranes can be constructed, for example, as flat membranes or as hollow-fibre membranes. Hollow-fibre membranes can be used in a "dead end" configuration or in "crossflow" configuration. These embodiments and their preparation are known to those skilled in the art.

SUMMARY OF THE INVENTION

It has been found that, advantageously, using anion-exchange membranes disclosed in WO 96/22 316 and WO 97/49 754, the said contaminants can be removed from solutions. Thus it has been found that endotoxin can be removed not only from a buffer solution but also from a solution of proteins. It has further been found that DNA (HindIII fragments of DNA of phage λ can be removed from protein. It has also been found that viruses can be removed from solutions, including viruses which can be removed only inadequately by known methods, for example by nano-filtration.

The invention relates to processes for the removal or depletion of biological contaminants, the sample to be cleaned up (biological product) being treated with an anion-exchange membrane, the said anion-exchange membrane being obtainable by reaction of a polyamide with an amino-reactive polymerizable compound and subsequent polymerization with monomers which comprise cationic groups, or into which cationic groups can be introduced in a polymer-analogous reaction.

The invention further relates to cleaned-up biological products obtainable by the process of the invention.

DETAILED DESCRIPTION OF THE INVENTION

Figure 1:
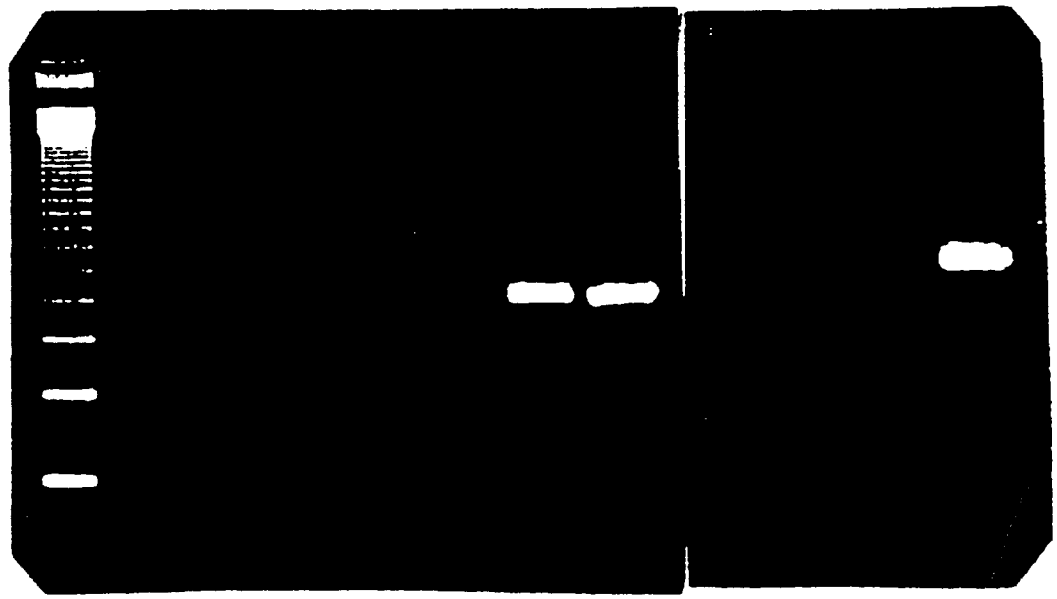
FIG. 1 shows PCR studies of various eluates which have been produced during the depletion of DNA.

The inventive removal of the contaminants is performed using buffer systems as are customary for anion-exchange chromatography. If required, neutral salts, organic solvents, detergents and/or chaotropic agents can be added to the buffers. Addition of this type are known to those skilled in the art and are described in the literature.

Even without further details, it is assumed that a person skilled in the art can use the above description to the broadest extent. The preferred embodiments and examples are therefore to be considered only as a descriptive disclosure, but in no sense as a disclosure limiting in any way.

The complete disclosure of all applications, patents and publications mentioned hereinbefore and hereinafter and of the corresponding application DE 198 10 947 4, filed on Mar. 13, 1998, are incorporated by reference into this application.

EXAMPLES

Examples 1–3

Depletion of Various Viruses

The depletion of various viruses was carried out by the company Ana/lysis (Frankfurt (Main), Del.) in accordance with current validation provisions ("Anforderungen an Validierungsstudien zum Nachweis der Virussicherheit von Arzneimitteln aus menschlichem Blut oder Plasma" [Requirements of validation studies for demonstrating the virus safety of medicinal products from human blood or plasma]; Paul-Ehrlich Institut and German Federal Health Agency, May 1994; and "Note for Guidance on Virus Validation Studies": CPMP/BWP/268/95; 2nd final version of February 1996). For the test, 20 mM TRIS buffer (pH 7.0) was mixed with 10% by volume of a virus stock solution; the following viruses were used:

HIV-1 Human immunodeficiency virus type 1
PPV Porcine parvovirus
BVDV Bovine viral diarrhoea virus Other data on the viruses used and relating to the virus-susceptible host cells and indicator cells are summarized in Table 1 below:

TABLE 1

|  | HIV-1 | PPV | BVDV |
|---|---|---|---|
| Strain | Bru | NADL-2 | RKI |
| Origin | Georg-Speyer-Haus | ATCC VR-742 | Robert-Koch-Institut |
| Host/indicator cells | C8166-45 cells[1] | PK-13 cells[2] | KL-2 cells[3] |

Notes:
[1]Human umbilical lymphocytes transformed with HTLVI (Georg-Speyer-Haus; Chemotherapeutisches Forschungs-institut, Frankfurt am Main, DE)
[2]Pig cells (European Collection of Animal Cells; Porton Down, Salisbury, UK)
[3]Fetal calf lung cells (Robert-Koch-Institut)

Notes:
(1) Human umbilical lymphocytes transformed with HTLVI (Georg-Speyer-Haus; Chemotherapeutisches Forschungs-institut, Frankfurt am Main, Del.)
(2) Pig cells (European Collection of Animal Cells; Porton Down, Salisbury, UK)
(3) Fetal calf lung cells (Robert-Koch-Institut)

10 ml of each of these solutions was applied using a syringe to a Fractoflow® 80-6 mm dead end hollow-fibre module (base material nylon 6; Merck KGBA, Darmstadt, Del.). The following types of anion-exchange hollow-fibre modules were used:

D weak anion exchanger (DEA type)
T strong anion exchanger (TMA type)

For comparison, modules having unmodified membranes and modules having cation-exchange membranes were used:

U underivatized nylon 6 base material
S strong cation exchanger (sulfo type)

Virus titres were determined by end-point titration before and after filtration. For this purpose serial three-fold dilutions of the sample were prepared, in each case in eight-fold replicates. The diluted samples were added to virus-susceptible indicators cells, and the incubated indicator cells were examined micro-scopically for cytopathic effects (CPE). Statistical analysis was performed by standard methods.

Example 1

Depletion of HIV-1

The depletion of HIV-1 was studied in accordance with the above general method description; the results are summarized in Table 2:

TABLE 2

| Module type | Log stage removal |
|---|---|
| T | ≧6.08· |
| D | ≧6.08· |
| U | 3.98 |
| S | 4.46 |

·No infectious material was detectable.

In the case of the use according to the invention of anion-exchange membranes, depletion to below the limit of detection was achieved, whereas in the comparison tests (U and S) a depletion which was lower by one to two orders of magnitude was observed.

Example 2

Depletion of porcine parvovirus

The depletion of PPV was studied in accordance with the above general method description; the results are summarized in Table 3:

TABLE 3

| Module type | Log stage removal |
|---|---|
| T | ≧6.84· |
| D | ≧6.84· |
| U | —# |
| S | —# |

·no infectious material was detectable;
no depletion could be measured.

In the case of the inventive use of anion-exchange membranes, depletion to below the limit of detection was achieved, whereas in the comparison tests (U and S) no depletion was observed. Porcine parvovirus is very small (approximately 20 nm) and very stable. This virus could not be removed completely by any previously known partition method.

The results obtained here show that the viruses were removed highly specifically only with the anion exchangers.

Example 3

Depletion of Bovine Viral Diarrhoea Virus

The depletion of BVDV was studied in accordance with the above general method description; the results are summarized in Table 4:

TABLE 4

| Module type | Log stage removal |
|---|---|
| T | 5.87 |
| D | ≧5.88· |
| U | 1.04 |
| S | 0.32 |

·no infectious material was detectable.

In the case of the inventive use of anion-exchange membranes, depletion to below the limit of detection was achieved, whereas in the comparison tests (U and S) a depletion which was lower by several orders of magnitude was observed.

The results obtained here show that the viruses are removed highly specifically only with the anion exchangers.

Example 4

Removal of Endotoxins

Material and Methods:

An 80-6 mm Fractoflow® DEA hollow-fibre module (Merck KGaA; Darmstadt, Del.) was used.

Samples were applied using a syringe.

The endotoxin activity was determined using the LAL test.

a) Removal from Buffer Solution

Sample: *E. coli* Endotoxin (USP Standard) in 20 mM Phosphate Buffer (pH 7)

The results of the removal of endotoxin from buffer solution are summarized in Table 5:

TABLE 5

| Solution | Endotoxin (EU/ml) | Endotoxin (% of the starting solution) |
|---|---|---|
| Starting solution | 1536 | 100 |
| Eluate cycle 1 | 3.9 | 0.25 |
| Eluate cycle 2 | 0.03[*] | 0.002 |

[*]Limit of detection

The endotoxin is removed from a buffer solution by three cycles to below the limit of detection of the LAL test.

b) Removal from Proteinaceous Solution

Sample: *E. coli* Endotoxin (USP Standard; 15 724 EU/ml) and Bovine Serum Albumin (BSA; 1 mg/ml) in 20 mM Phosphate Buffer (pH 7)

BSA eluted with 0.4 M NaCl in 20 mM phosphate buffer (pH 7).

The results of removing endotoxin from a 1 mg/ml BSA solution by selection desorption are summarized in Table 6:

TABLE 6

| Solution | Endotoxin (EU/ml) | Endotoxin (% of the starting solution) | Bovine serum albumin (BSA) (% recovery) |
|---|---|---|---|
| Starting solution | 15724 | 100 | 100 |
| Eluate cycle 1 | 422 | 2.7 | 95 |
| Eluate cycle 2 | 3.5 | 0.02 | 94 |

BSA and endotoxin may be separated by selective desorption of the albumin at 0.4 M sodium chloride.

Example 5

Removal of DNA

An 80-6 mm Fractoflow® DEA hollow-fibre module was used. The sample solution was applied using a syringe. 10 ml of a BSA solution having a concentration of 1 mg/ml in 20 mM Tris pH 8.5 were mixed with 1 μg of λDNA (cut using HindIII). After sample addition, the system was washed with 10 ml of buffer solution (20 mM Tris pH 8.5). The protein was eluted with 15 ml of a 20 mM Tris solution +1 M NaCl pH 8.5. The system was then washed again with 10 ml of a 20 mM Tris buffer pH 8.5.

BSA was bound under these conditions and was eluted by 1 M sodium chloride addition with a recovery of 97%. The DNA could not be detatched by 1 M sodium chloride and could be removed only with 2×10 ml of a 1 M sodium hydroxide solution.

Track 1: λ DNA
Track 2: Sample addition
Track 3: 20 mM Tris buffer (pH 8.5)
Track 4: 1 M NaCl in 20 mM Tris buffer (pH 8.5)
Track 5: 1 M NaOH
Track 6: 1 M NaOH For tracks 7, 8, 9, 10 and 11, further eluates with 6 M urea, 20 mM Tris, 6 M guanidinium chloride, 20 mM Tris, ethanol were used.

In the various eluates, the DNA was detected by PCR as follows:

Reagent mixture (Mix):

| 10 × polymerase buffer | 20 μl |
|---|---|
| dNTPs (20 mM) | 2 μl |
| Primer λ1 (5 pmol/μl) | 8 μl |
| Primer λ2 (5 pmol/μl) | 8 μl |
| Taq polymerase (5 U/μl) | 2 μl |
| Water | 80 μl |

15 μl of the above reagent mixture and 10 μl of sample (the respective eluate; 1–11) were mixed; the polymerase chain reaction (PCR) was then carried out and the reaction products detected by electrophoresis:

PCR Programme:
 3 min, 94° C.
 10×
  15 sec, 92° C.
  15 sec, 65°C. (−1° C./cycle)
 10×
  15 sec, 92°C.
  15 sec, 55°C.
 5 min, 72° C. to end Detection by Electrophoresis:
 addition of 5 μl of dye marker
 10 μl in each case on 2% Hispan agarose gel
 Comparison: 10 μl of marker (λ DNA; cut with HindIII)

The results are shown in FIG. 1. In the elution with NaOH, 90% of the DNA was recovered.

In a further experiment, it was found that the DNA depletion can be performed even in the presence of 1 M sodium chloride in the protein solution.

To verify the sensitivity of detection of the PCR method used, a stock solution of λ DNA (HindIII fragments) in a 1:10 serial dilution was subjected to the same method:

| | Sample No.: | | | | | | |
|---|---|---|---|---|---|---|---|
| | 1 | 2 | 3 | 4 | 5 | 6 | 7 |
| Mix (μl) | 15 | 15 | 15 | 15 | 15 | 15 | 15 |
| λ HindIII[*] (μl) | 10 | 10 | 10 | 10 | 10 | 10 | 10 |
| DNA quantity | 100 pg | 10 pg | 1 pg | 100 fg | 10 fg | 1 fg | 100 ag |

Figure 2:
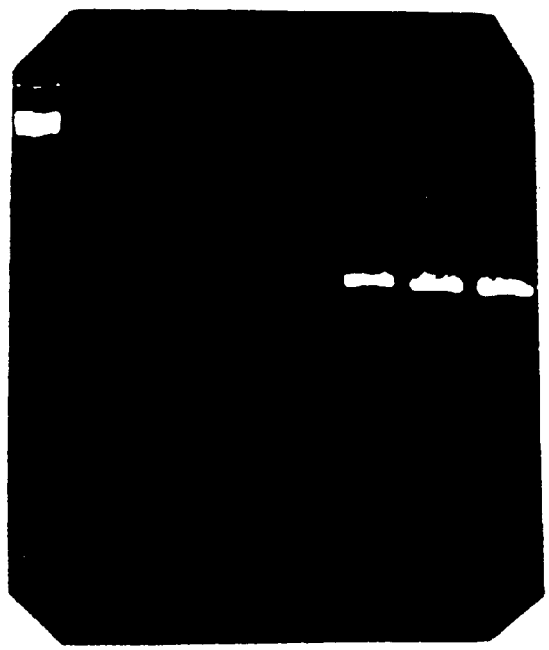
FIG. 2 shows the sensitivity of detection of the PCR method used; experimental details may be found in Example 5.

[*]Initial concentration 100 pg/μl; 1:10 serial dilutions; dilution 7 (100 attograms) corresponds to 2–3 DNA molecules left The results are shown in FIG. 2.

Even without further details, it is assumed that a person skilled in the art can use the above description to the broadest extent. The preferred embodiments and examples are therefore to be considered only as a descriptive disclosure, but in no sense as a disclosure limiting in any way.

The complete disclosure of all applications, patents and publications mentioned hereinbefore and hereinafter are incorporated by reference into this application.

What is claimed is:

1. A process for the removal or depletion of biological contaminants from biological products, comprising treating a sample with an anion exchanger membrane, which is obtainable by reaction of a polyamide with an aminoreactive polymerizable compound and subsequent polymerization with monomers containing cationic groups, or monomers into which cationic groups are subsequently introduced.

2. The process according to claim 1, wherein viruses are removed from the sample.

3. The process according to claim 1, wherein nucleic acids are removed from the sample.

4. The process according to claim 1, wherein endotoxins are removed from the sample.

5. A process for the removal or depletion of biological contaminants from biological products, comprising treating a sample with an anion exchanger membrane, which is obtained by reaction of a polyamide with an amino-reactive polymerizable compound and subsequent polymerization with monomers containing cationic groups, or monomers into which cationic groups are subsequently introduced.

* * * * *